United States Patent
Nakaoka et al.

(10) Patent No.: US 6,620,145 B2
(45) Date of Patent: Sep. 16, 2003

(54) DISPOSABLE DIAPER

(75) Inventors: Kenji Nakaoka, Tokushima (JP);
Masaru Fujioka, Tokushima (JP);
Satoshi Maeda, Tokushima (JP);
Kazuyo Mori, Tokushima (JP)

(73) Assignee: Toyo Eizaki Kabushiki Kaisha, Ehime (JP)

( * ) Notice: Subject to any disclaimer, the term of this patent is extended or adjusted under 35 U.S.C. 154(b) by 0 days.

(21) Appl. No.: 09/890,287

(22) PCT Filed: Nov. 30, 2000

(86) PCT No.: PCT/JP00/08483
§ 371 (c)(1),
(2), (4) Date: Jul. 27, 2001

(87) PCT Pub. No.: WO01/39714
PCT Pub. Date: Jun. 7, 2001

(65) Prior Publication Data
US 2002/0138060 A1 Sep. 26, 2002

(30) Foreign Application Priority Data
Nov. 30, 1999 (JP) .............................. 11-340659

(51) Int. Cl.$^7$ .............................. A61F 13/20; A61F 13/15
(52) U.S. Cl. .............................. 604/385.28; 604/385.14; 604/385.21; 604/385.27; 604/394
(58) Field of Search ................. 604/385.14, 385.19, 604/385.21–385.3, 393–398, 385.03, 402

(56) References Cited

U.S. PATENT DOCUMENTS

| | | | | |
|---|---|---|---|---|
| 4,704,116 A | * | 11/1987 | Enloe ................. | 604/585.28 |
| 4,795,454 A | * | 1/1989 | Dragoo ................. | 604/385.27 |
| 4,816,025 A | * | 3/1989 | Foreman ................. | 604/385.27 |
| 5,344,516 A | * | 9/1994 | Tanji et al. ............ | 604/385.19 |
| 5,403,301 A | * | 4/1995 | Huffman et al. ......... | 604/385.28 |
| 5,584,828 A | * | 12/1996 | Yamamoto et al. ..... | 604/385.28 |
| H1630 H | * | 1/1997 | Roe et al. ............. | 604/385.28 |
| 5,613,959 A | * | 3/1997 | Roessler et al. ....... | 604/385.28 |
| 5,672,166 A | * | 9/1997 | Vandemoortele ....... | 604/385.28 |
| 6,186,996 B1 | * | 2/2001 | Martin ................. | 604/385.19 |
| 2001/0037103 A1 | * | 11/2001 | Onishi ................. | 604/385.19 |

\* cited by examiner

*Primary Examiner*—Karin Reichle
(74) *Attorney, Agent, or Firm*—Jordan and Hamburg LLP

(57) ABSTRACT

Elastic threads for raisable gathers and elastic threads for leg gathers are provided in a specified relationship in side sheets provided at the opposite sides of a skin-side sheet, and the respective side sheets are adhered to the skin-side sheet in a specified relationship. In this way, the raisable gathers and leg gathers can be simultaneously formed in the side sheets. Further, a pocket into which an exchangeable and substantially sandglass-shaped second absorbent body can be positioned and inserted is formed between the skin-side sheet enclosed by the respective adhered portions and the respective side sheets.

2 Claims, 6 Drawing Sheets

DISPOSABLE DIAPER

BACKGROUND OF THE INVENTION

The present invention relates to a disposable diaper having a simple structure and usable with an exchangeable absorbent body.

Conventionally, there is a disposable diaper in which an absorbent body is provided between an outer sheet and a skin-side sheet. Raisable strips for preventing lateral leakage of urine and other bodily waste are provided at opposite sides of the absorbent body on the skin-side sheet. Side sheets are provided between the raisable strips and the skin-side sheet so as to extend outwardly from the outer side edges of the skin-side sheet.

In the above prior art disposable diaper, the raisable strips and the side sheets are separately provided. Raisable gathers are formed by elastic threads provided at the inner side edges of the raisable strips. Leg gathers are formed by elastic threads provided at the outer edge portions between the outer sheet and the skin-side sheet.

The prior art disposable diaper is used on the condition that it is exchanged regardless of a urinated amount. However, in the case of lesser urinated amount and frequent incontinences, an exchangeable absorbent body has been used and is placed on the raisable strips in order to save the trouble of exchanging the diaper and make the diaper more economical.

However, the structure and manufacturing process are problematic due to the complicated nature thereof the raisable strips and the side sheets are separately provided, the elastic threads for the raisable gathers are provided at the raisable strips, and the elastic threads for the leg gathers are provided between the outer sheet and the skin-side sheet.

Further, since the exchangeable absorbent body is placed on the raisable strips, it may be displaced or prevent the raisable strips from raising, with the result that urine or other bodily waste may laterally leak to stain clothes.

In view of the problems residing in the prior art, an object of the present invention is to provide a disposable diaper which has a simple structure, can be manufactured by a simple process, and can effectively prevent displacement and a lateral leakage of urine and other bodily waste even if an exchangeable absorbent body is used.

DISCLOSURE OF THE INVENTION

The present invention is directed to a disposable diaper, wherein a first absorbent body is provided between an outer sheet and a skin-side sheet; side sheets are provided at the opposite sides of the upper surface of the skin-side sheet; elastic threads for raisable gathers are provided along the inner edge portions of the respective side sheets substantially over the entire length of the side sheets; elastic threads for leg gathers are provided at part of the outer edge portions of the respective side sheets near leg portions; the respective side sheets are adhered to the skin-side sheet substantially over the entire length of the side sheets at a position outwardly of the elastic threads for the leg gathers while being adhered thereto along a line substantially over the entire length of the elastic threads for the leg gathers at a position inwardly of the elastic threads for the leg gathers; and front and rear end portions of the respective side sheets are adhered to the skin-side sheet.

According to the present invention, the raisable gathers and the leg gathers can be simultaneously formed in the respective side sheets by providing the elastic threads for the raisable gathers and those for the leg gathers in a specified relationship relative to the respective side sheets provided at the opposite sides of the skin-side sheet and adhering the respective side sheets to the skin-side sheet in a specified relationship.

BEST MODE FOR CARRYING OUT THE INVENTION

Figure 1:
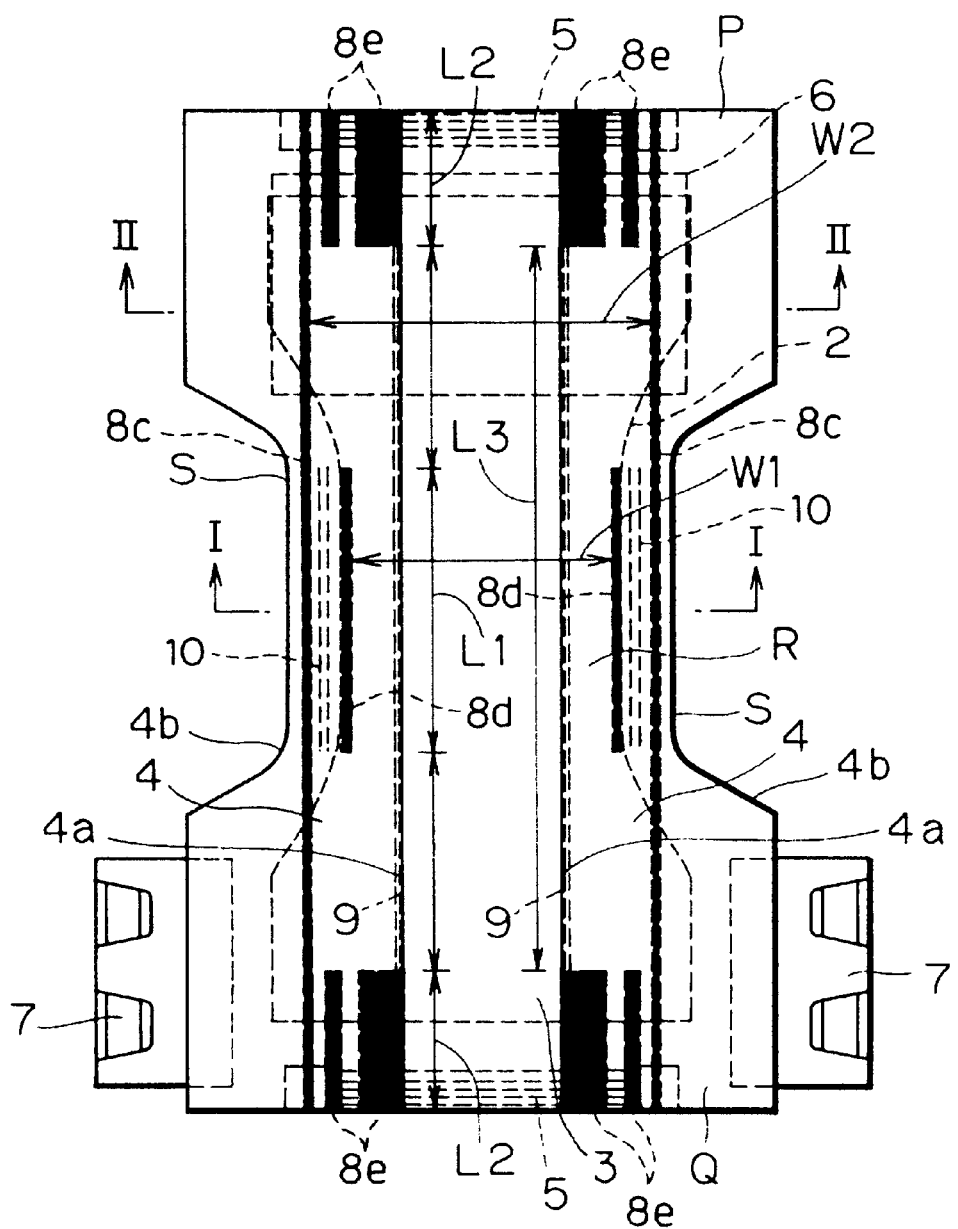
FIG. 1 is a front view of an inventive disposable diaper in its developed state.
Figure 2A:
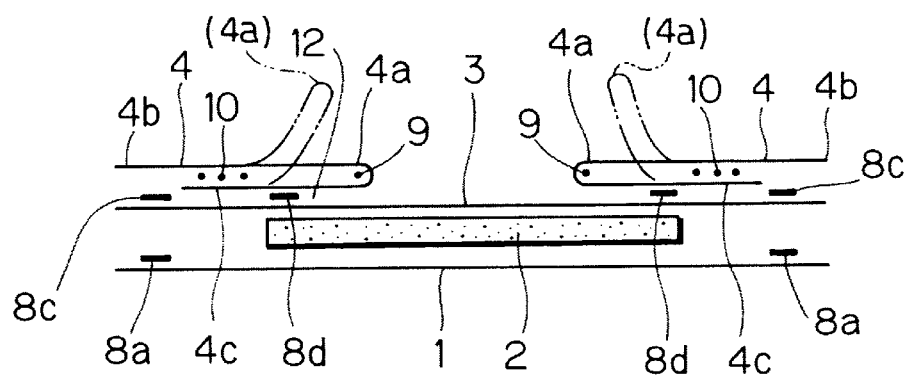
FIGS. 2A and 2B are a schematic section along I—I of FIG. 1 and a schematic section along II—II of FIG. 1.
Figure 2B:
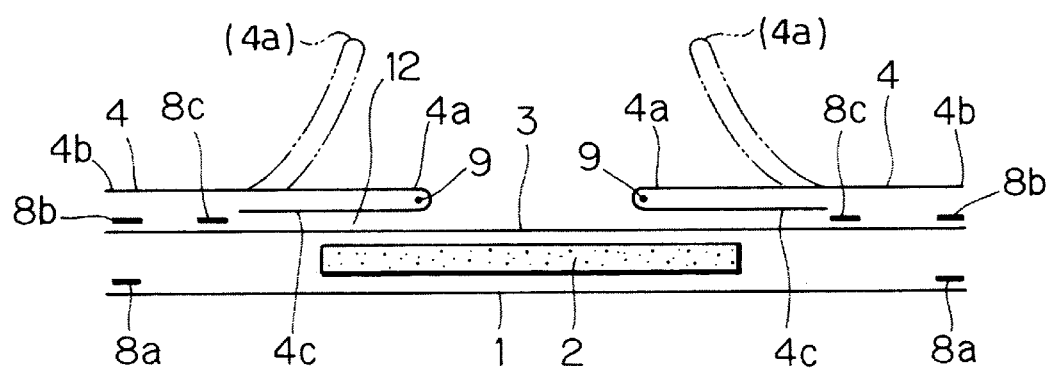
Figure 3:
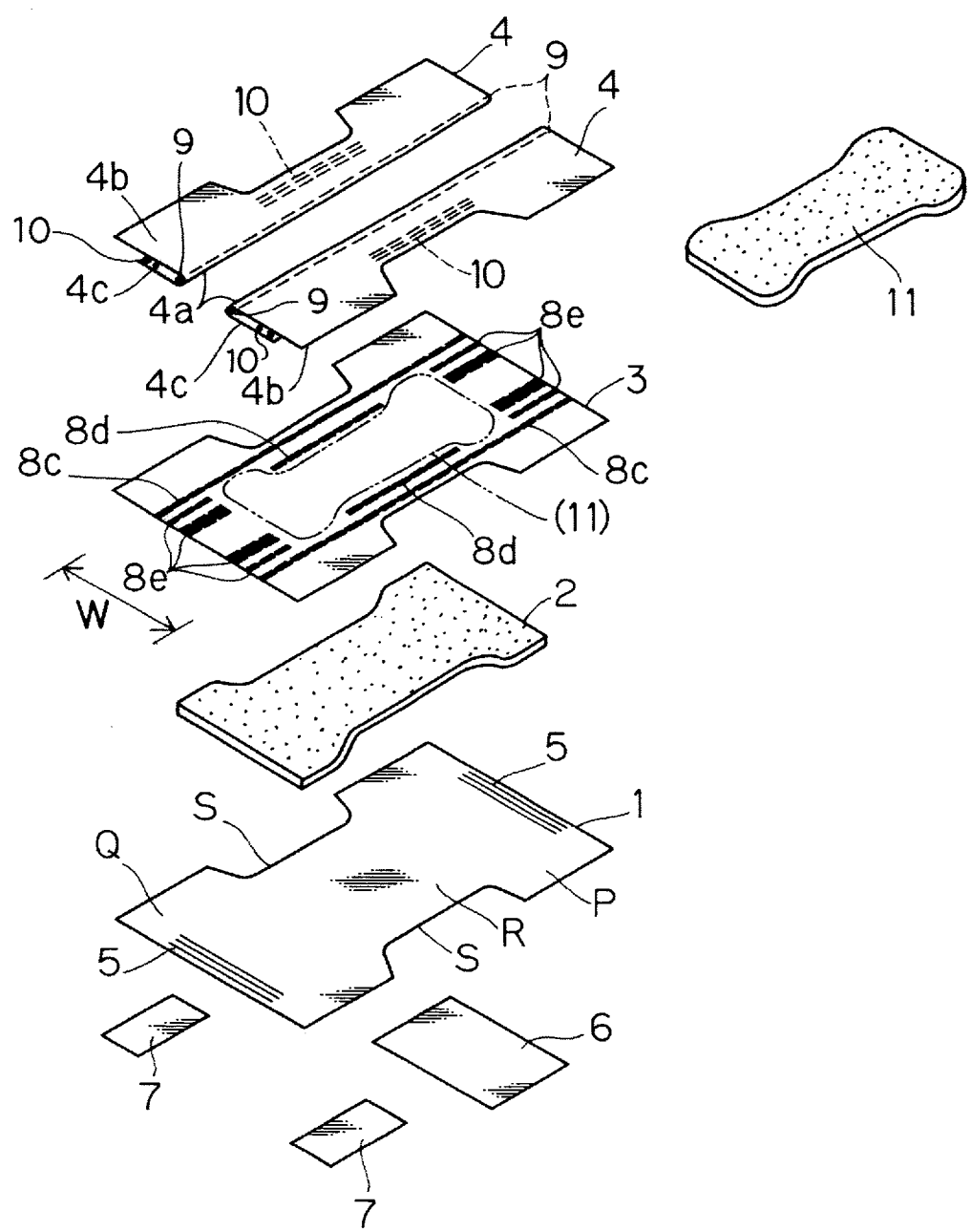
FIG. 3 is an exploded perspective view of the disposable diaper.
Figure 4:
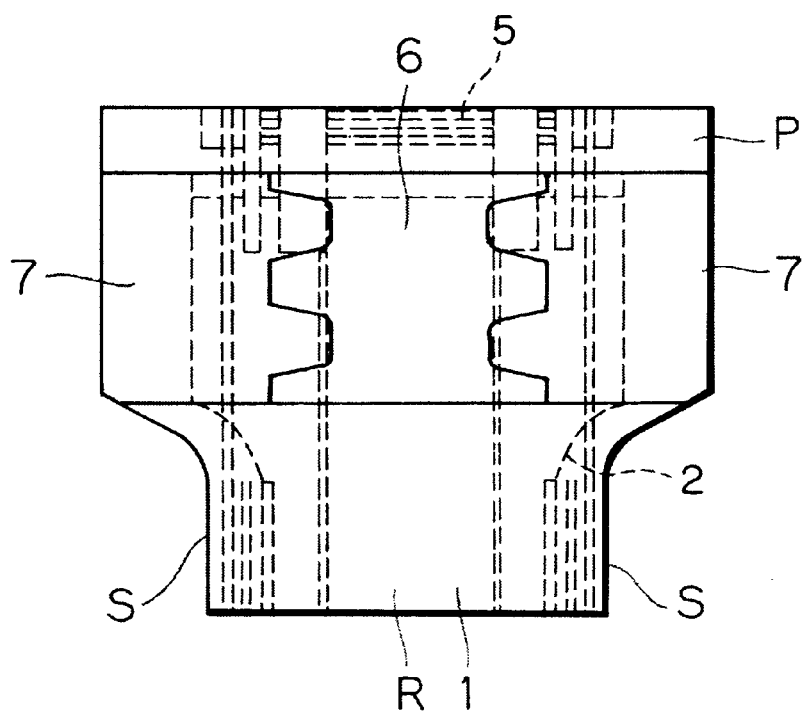
FIG. 4 is a front view of the disposable diaper in its used state.

Hereinafter, one embodiment of the present invention is described in detail with reference to the accompanying drawings. FIG. 1 is a front view of an inventive disposable diaper in its developed state. FIGS. 2A and 2B are a schematic section along I—I of FIG. 1 and a schematic section along II—II of FIG. 1. FIG. 3 is an exploded perspective view of the disposable diaper. FIG. 4 is a front view of the disposable diaper in its used state.

As shown in FIG. 3, a disposable diaper is basically comprised of an outer sheet 1, a first absorbent body 2, a skin-side sheet 3, and a pair of left and right side sheets 4.

The outer sheet 1 is formed of a nonwoven fabric made of a synthetic resin having water repellency or a synthetic resin film, and leg openings S are formed at the opposite sides of a crotch portion R between a front part P and a rear part Q.

A plurality of elastic threads 5 for waist gathers are provided on the upper surfaces of the front and rear parts P, Q of the outer sheet 1 while being stretched in widthwise direction.

Further, a frontal tape 6 is attached to the lower surface of the front part P of the outer sheet 1, and fastening tapes 7 are attached to the opposite sides of the lower surface of the rear part Q so as to assemble the disposable diaper in a 3D manner by being adhered to the frontal tape 6 as shown in FIG. 4 when the disposable diaper is used.

The first absorbent body 2 is formed of a mixture of natural pulp fibers, synthetic resin fibers and a high water-absorbent polymer material or by laminating these materials, and is a flat member which is about one size smaller than the outer sheet 1, substantially in the form of a sandglass or rectangle and wrapped in a tissue paper. This first absorbent body 2 is adhered to the upper surface of the outer sheet 1.

The skin-side sheet 3 is formed of a nonwoven fabric made of a synthetic resin having hydrophilic properties and has the same outer configuration as the outer sheet 1. The lower surface of the skin-side sheet 3 and the upper surface of the outer sheet 1 are suitably adhered by adhesive 8a (see FIGS. 2A and 2B), etc. with the first absorbent body 2 and the elastic threads 5 provided therebetween. The skin-side sheet 3 has a rectangular portion having such a width (see FIG. 3) as to enable application of adhesive 8c.

The left and right side sheets 4 are formed of a nonwoven fabric made of a synthetic resin having water repellency, have substantially the same length as the outer sheet 1 and the skin-side sheet 3, and are formed at portions corresponding to the leg openings S with leg openings having the same shape.

Inner portions of the respective side sheets 4 are deeply folded back downwardly and inwardly, and inner edge portions 4a of these folded portions 4c cover the opposite sides of the upper surface of the first absorbent body 2. Further, at the front and rear parts P, Q, the lower surfaces of outer edge portions 4b of the side sheets 4 are suitably adhered to the upper surface of the skin-side sheet 3 by adhesive 8b (see FIG. 2B).

At the inner edge portions 4a of the folded portions 4c of the respective side sheets 4, elastic threads 9 are provided substantially over the entire length of the side sheets 4 to form raisable gathers while being stretched. In the vicinity of the ends of the folded portions 4c, a plurality of elastic threads 10 are adhered at positions of the outer edge portions 4b near the leg openings S to form leg gathers while being stretched. In this way, the elastic threads 9, 10 for the raisable gathers and leg gathers, respectively are held between the folded portions 4c of the side sheets 4 and remembers of the side sheets 4.

The respective elastic threads 5, 9, 10 are made of strip-shaped or thread-shaped natural rubber or synthetic rubber, and the waist gathers, raisable gathers and leg gathers are naturally formed by the shrinking force of the elastic threads 5, 9, 10.

The respective side sheets 4 are adhered to the upper surface of the skin-side sheet 3 by the adhesive 8c (see FIGS. 1, 2A, 2B and 3) along lines extending substantially over the entire length of the side sheets 4 at positions close to the outer edge portions 4b of the side sheets 4 and immediately outwardly of the elastic threads 10. The respective side sheets 4 are also adhered to the upper surface of the skin-side sheet 3 by adhesive 8d (see FIGS. 1, 2A and 3) along lines extending substantially over the entire length of the elastic threads 10 at positions close to the inner edge portions 4a of the side sheets 4 and immediately inwardly of the elastic threads 10. It should be noted that the "lines" include dotted lines.

The portions adhered by the adhesives 8c, 8b (see FIG. 2B) may need not be separate. Adhesive may be applied to entire areas between these portions adhered by the adhesives 8c, 8b or intermittently applied to these areas in a dotted or spiral manner.

Specifically, the respective side sheets 4 are adhered to the skin-side sheet 3 along the lines extending substantially over the entire length of the side sheets 4 at the positions immediately outwardly of the elastic threads 10 while being adhered thereto along the lines extending substantially over the entire length of the elastic threads 10, i.e. over a short length L1 at the positions immediately inwardly of the elastic threads 10.

Figure 5:
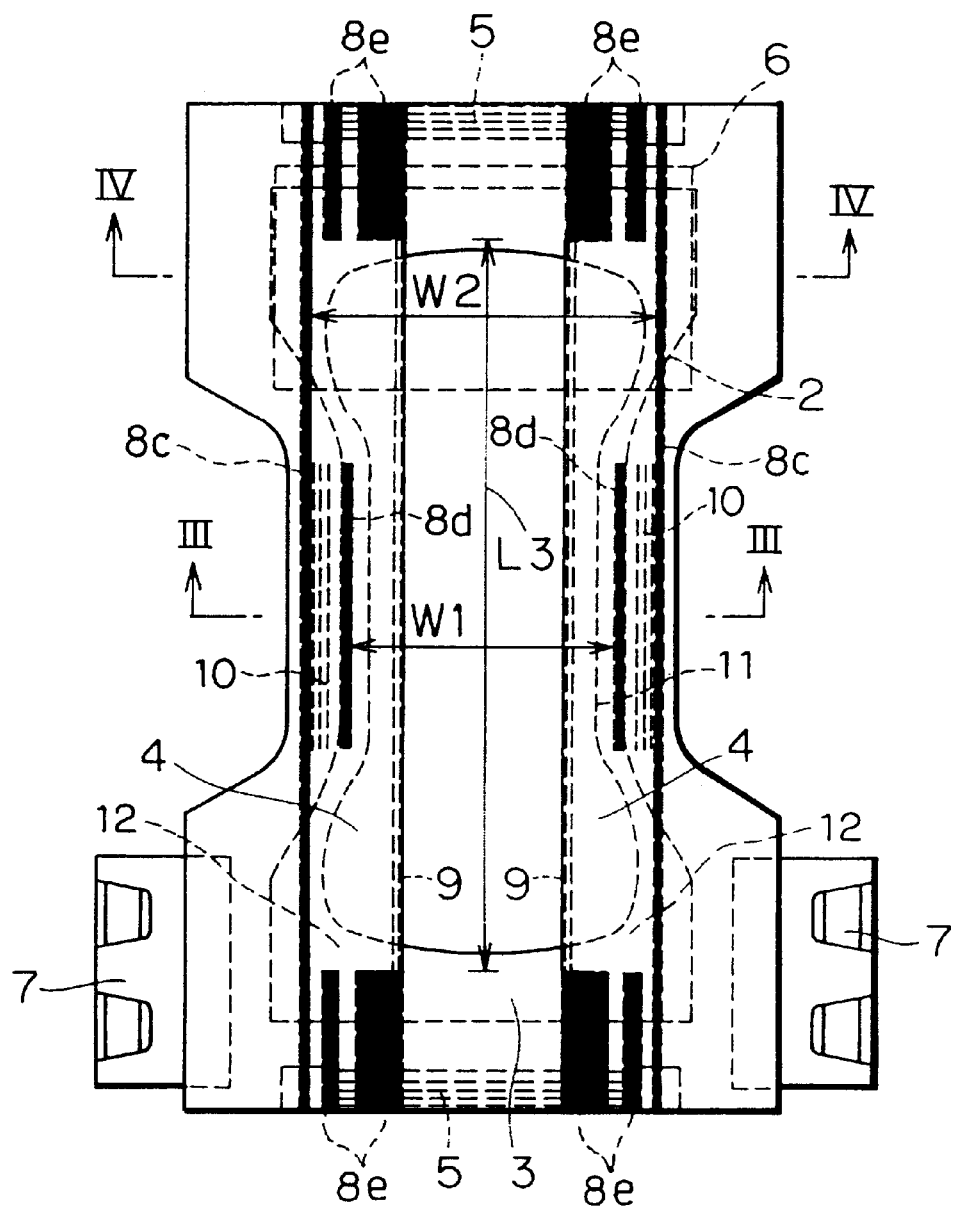
FIG. 5 is a front view of the disposable diaper in its developed state where a second absorbent body is inserted.

The lower surfaces of the front and rear ends of the respective side sheets 4 are intermittently adhered to the upper surface of the skin-side sheet 3 by adhesive 8e (see FIGS. 1, and 3) over such a short length L2 that these lower surfaces only slightly overlap the front and rear ends of the first absorbent body 2. Thus, the front and rear ends of the side sheets 4 are not raisable. In FIGS. 1, 3 and 5, the adhesives 8c, 8d, 8e are shown particularly in black in order to clarify the positions and widths thereof (8b is not shown).

Figure 6A:
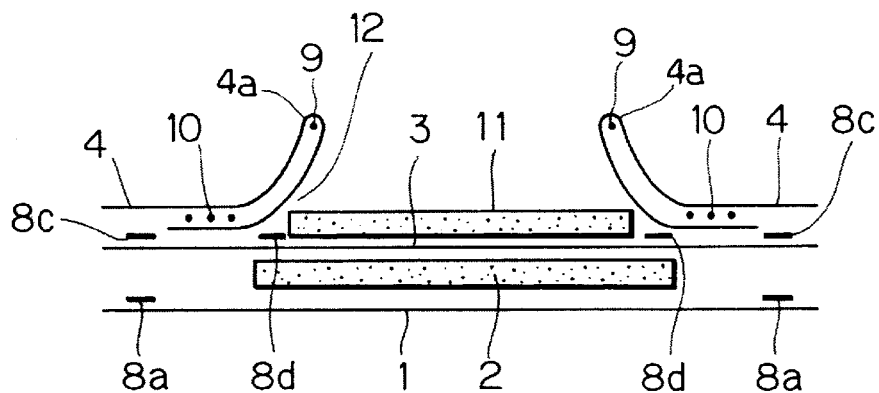
FIGS. 6A and 6B are a schematic section along III—III of FIG. 5 and a schematic section along IV—IV of FIG. 5.
Figure 6B:
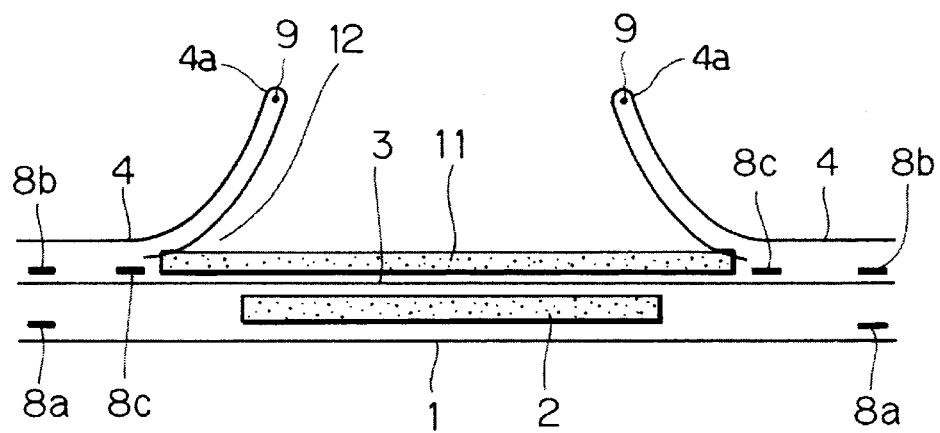

By the aforementioned linear adhesion by the adhesive 8c over the entire length of the side sheets 4, linear adhesion by the adhesive 8d over the length L1, and intermittent adhesion by the adhesive 8e over the length L2, a pocket 12 which has widths W1, W2 and a length L3 and into which a second absorbent body 11 can be exchangeably positioned and inserted is formed between the skin-side sheet 3 the portions adhered by the respective adhesives 8c to 8e and the respective side sheets 4 as shown in FIGS. 5 and 6.

Similar to the first absorbent body 2, the second absorbent body 11 is formed of a mixture of natural pulp fibers, synthetic resin fibers and a high water-absorbent polymer material or by laminating these materials, and is a flat member which is about one size smaller than the first absorbent body 1, substantially in the form of a sandglass and wrapped in a tissue paper. The second absorbent body 11 needs not be in the form of a sandglass, and may be rectangular shaped provided that it can be positioned in the pocket 12.

In the disposable diaper thus constructed, the elastic threads 9 for the raisable gathers and the elastic threads 10 for the leg gathers are so provided in the side sheets 4 as to have the above relationship, and the side sheets 4 are adhered to the skin-side sheet 3 in the above relationship. Accordingly, the inner edge portions 4a of the side sheets 4 are raised within a range of a length L3 by the shrinkage of the elastic threads 9 for the raisable gathers (see chain double-dashed line in FIGS. 2A and 2B) and, at the same time, the leg gathers are formed near the leg openings S within a range of the length L1 by the shrinkage of the elastic threads 10.

Thus, unlike the prior art, the separate raisable strips are unnecessary, simplifying the structure of the diaper, and the manufacturing process can also be simplified since it is sufficient to provide the elastic threads 9 and 10 only in the side sheets 4.

Further, as shown in FIGS. 5 and 6, the pocket 12 is formed between the skin-side sheet 3 and the side sheets 4, and the second absorbent body 11 can be exchangeably inserted into this pocket 12. Thus, this disposable diaper is economical because it is sufficient to exchange only the second absorbent body 11 in the case of a small amount of urine or other bodily waste, and can effectively prevent a lateral leak of urine and other bodily waste since the urine and the like leaked from the second absorbent body 11 can be absorbed by the first absorbent body 2 even in the case of a large amount of urine or other bodily waste.

In this case, the pocket 12 has the width W1, the width W2 longer than W1 and the length L3, L and forms a sandglass-shaped space. By positioning and inserting the sandglass-shaped second absorbent body 11 which is wider at its front and rear ends and narrower in the middle into the pocket 12, the absorbent body 11 is displaceable neither along the widthwise direction nor along the lengthwise direction.

Further, since the raisable gathers are formed at the opposite sides of the second absorbent body 11 inserted into the pocket 12 by the respective side sheets 4, there is no danger of lateral leakage of urine and other bodily waste.

Although the invention is applied to the disposable diaper in the foregoing embodiment, it is, of course, also applicable to disposable underpants in which the first absorbent body is mounted on the skin-side sheet which is placed on the outer sheet.

As is clear from the above description, according to the present invention, the raisable gathers and the leg gathers can be simultaneously formed in the respective side sheets by providing the elastic threads for the raisable and leg gathers in the specified relationship in the respective side sheets provided at the opposite sides of the skin-side sheet. Thus, raisable strips are unnecessary, the structure can be simplified, and the manufacturing process can be simplified since it is sufficient to provide the elastic threads for the raisable and leg gathers only in the side sheets.

Further, since the pocket into which the exchangeable second absorbent body, preferably the sandglass-shaped second absorbent body is positioned and inserted is formed between the skin-side sheets, the respective adhered portions and the respective side sheets, the second absorbent body can be exchangeably inserted into this pocket so as not to be displaced. Since the raisable gathers are formed at the opposite sides of the inserted second absorbent body by the respective side sheets, urine and other bodily waste can be effectively prevented from laterally leaking.

As described above, the inventive disposable diaper is useful as disposable diapers usable with exchangeable absorbent bodies or disposable underpants.

What is claimed is:

1. A disposable diaper comprising:

a first absorbent body provided between an outer sheet and a skin-faceable sheet, side sheets provided at respective opposite sides of an upper surface of the skin-faceable sheet, said side sheets each having front and rear parts and an intermediate portion between said front and rear parts said intermediate portions adapted to face legs of a wearer, first elastic threads for raisable gathers provided along inner edge portions of the respective side sheets over substantially the entire length of the side sheets, second elastic threads for leg gathers provided only at outer edge portions of the respective side sheets adjacent said intermediate portion and extending along substantially the entire length thereof, the respective side sheets being adhered to the skin-faceable sheet at a first adherence part over substantially the entire length of the side sheets at a position outwardly of the second elastic threads for the leg gathers, the respective side sheets also being adhered to the skin-faceable sheet at a second adherence part extending only over substantially the entire length of the second elastic threads for the leg gathers at a position inwardly of the second elastic threads for the leg gathers but outwardly of said first elastic thread whereby the length of the second adherence part is less than the length of the first adherence part and front and rear end portions of the respective side sheets being adhered to the skin-faceable sheet such that a pocket is thereby formed between the skin-faceable sheet and the side sheets, and a replaceable second absorbent body disposed in said pocket, said second absorbent body being sized and shaped complementary to the pocket whereby lateral and longitudinal displacement of the second body and lateral leakage from said second body are prevented.

2. The disposable diaper according to claim 1, wherein the second absorbent body is sandglass-shaped is less than the length of the first elastic threads.

* * * * *